United States Patent
Uchikawa et al.

(10) Patent No.: US 7,370,545 B2
(45) Date of Patent: May 13, 2008

(54) OXYGEN SENSOR

(75) Inventors: Akira Uchikawa, Gunma (JP); Futoshi Ichiyanagi, Gunma (JP); Masao Tsukada, Gunman (JP)

(73) Assignee: Hitachi, Ltd., Tokyo (JP)

( * ) Notice: Subject to any disclaimer, the term of this patent is extended or adjusted under 35 U.S.C. 154(b) by 23 days.

(21) Appl. No.: 11/582,412

(22) Filed: Oct. 18, 2006

(65) Prior Publication Data
US 2007/0089482 A1 Apr. 26, 2007

(30) Foreign Application Priority Data
Oct. 20, 2005 (JP) .............. 2005-306274

(51) Int. Cl.
*G01D 21/00* (2006.01)
(52) U.S. Cl. .................. 73/866.5
(58) Field of Classification Search .......... 73/23.31, 73/31.05, 866.5
See application file for complete search history.

(56) References Cited

U.S. PATENT DOCUMENTS 4,939,468 A * 7/1990 Takeuchi ............ 324/690
6,263,748 B1 * 7/2001 White ................. 73/866.5
2006/0272944 A1 * 12/2006 Ichiyanagi et al. ......... 204/424

FOREIGN PATENT DOCUMENTS

JP 11-337513 A 12/1999

* cited by examiner

*Primary Examiner*—Hezron Williams
*Assistant Examiner*—John Fitzgerald
(74) *Attorney, Agent, or Firm*—Antonelli, Terry, Stout & Kraus, LLP.

(57) ABSTRACT

An oxygen sensor includes a sensing element detecting an oxygen concentration in a measurement gas that flows in a pipe, a cylindrical protector which covers an outside of the sensing element and whose top end portion projects toward an inside of the pipe. An outside diameter D of the protector and a projection amount L of the protector inside the pipe are set so that a ratio of the product of the outside diameter D and the projection amount L (D×L) to a cross-sectional area S of a flow passage of the pipe becomes substantially smaller than or equal to 2.5%.

10 Claims, 2 Drawing Sheets

AMOUNT OF PROJECTION OF PROTECTOR L (mm)

OUTSIDE DIAMETER OF PROTECTOR D (mm)

OXYGEN SENSOR

BACKGROUND OF THE INVENTION

The present invention relates to an oxygen sensor which detects oxygen concentrations in measurement gas that flows in a pipe.

In recent years, there have been proposed and developed various oxygen sensors, and one oxygen sensor has been disclosed in Japanese Patent Provisional Publication No. 11-337513 (hereinafter is referred to as "JP11-337513"). In JP11-337513, an outside of a sensing element is covered with a protector, and this sensing element is inserted into an exhaust pipe with the sensing element covered in the protector. Then, these sensing element and protector are fixed to an inside of exhaust pipe such that exhaust gas flows into the protector from an inflow hole and touches the sensing element.

SUMMARY OF THE INVENTION

In the above oxygen sensor in JP11-337513, the exhaust gas contacts with the sensing element, and thereby electrically detecting the oxygen concentrations in the gas as a change of resistance value. However, in this type of oxygen sensor, in order to introduce the exhaust gas into an inside of the protector, the protector projects or protrudes inside the exhaust pipe. Because of this, in a case where an amount of projection of the protector inside the exhaust pipe is large, this becomes resistance of exhaust gas flow and affects exhaust efficiency. As a result, there is a possibility that this will lead to deteriorations in the fuel efficiency and power. However, if the projection amount is small so as to reduce the resistance of exhaust gas flow, it becomes difficult to sufficiently and adequately introduce the exhaust gas into the inside of protector.

It is therefore an object of the present invention to provide an oxygen sensor which is capable of securing the sufficient introduction amount of exhaust gas to detect the oxygen concentrations without increasing the gas flow resistance.

According to one aspect of the present invention, an oxygen sensor comprises a sensing element detecting an oxygen concentration in a measurement gas that flows in a pipe; a cylindrical protector which covers an outside of the sensing element and whose top end portion projects toward an inside of the pipe, and an outside diameter D of the protector and a projection amount L of the protector inside the pipe are set so that a ratio of the product of the outside diameter D and the projection amount L (D×L) to a cross-sectional area S of a flow passage of the pipe becomes substantially smaller than or equal to 2.5%.

According to another aspect of the invention, an oxygen sensor set inside an exhaust pipe for a motorcycle comprises a sensing element detecting an oxygen concentration in a measurement gas that flows in the exhaust pipe; a cylindrical protector which covers an outside of the sensing element and whose top end portion projects toward an inside of the exhaust pipe, and when an internal diameter of the exhaust pipe is smaller than or equal to 40 mm, an outside diameter D of the protector and a projection amount L of the protector inside the exhaust pipe are set so that a ratio of the product of the outside diameter D and the projection amount L (D×L) to a cross-sectional area S of a flow passage of the exhaust pipe becomes substantially smaller than or equal to 2.5%.

The other objects and features of this invention will become understood from the following description with reference to the accompanying drawings.

DETAILED DESCRIPTION OF THE INVENTION

Embodiments of the present invention will be explained below with reference to the drawings. In the embodiments, an oxygen sensor that is used inside an exhaust pipe of internal combustion engine will be explained as one example (Thus, as a matter of course, the oxygen sensor can be used inside not only the exhaust pipe but also any pipe).

Figure 1:
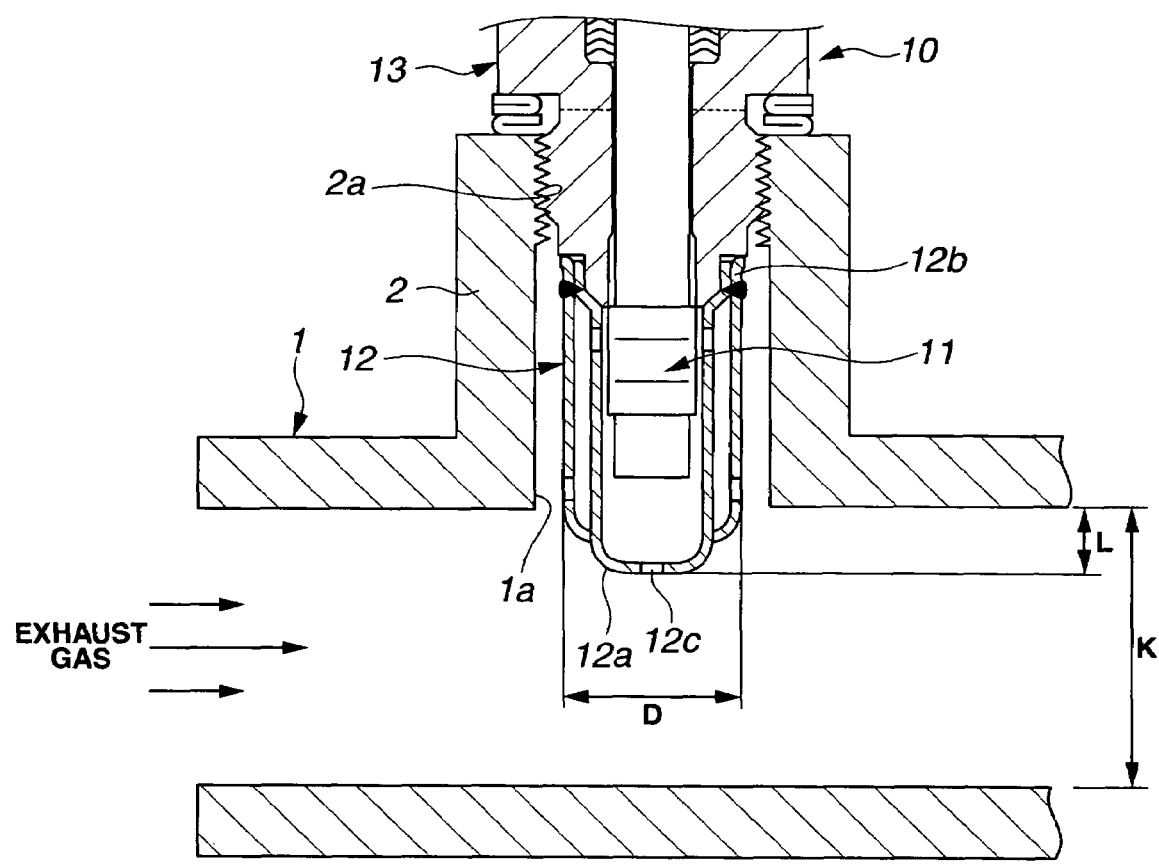
FIG. 1 is a sectional view of an oxygen sensor, under the state where the oxygen sensor is fixed to an exhaust pipe, according to one embodiment of the present invention.
Figure 2:
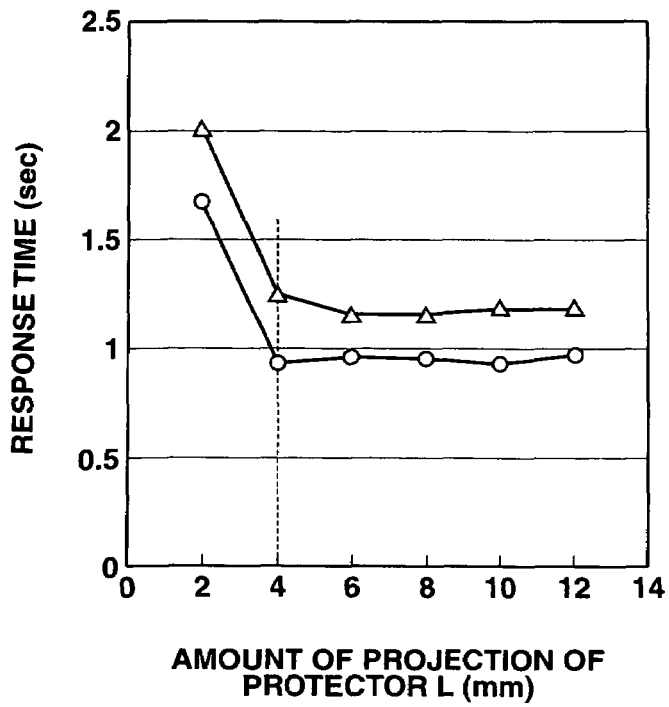
FIG. 2 is a drawing to explain a relationship between an amount of projection of a protector and response time of the oxygen sensor according to the one embodiment.
Figure 3:
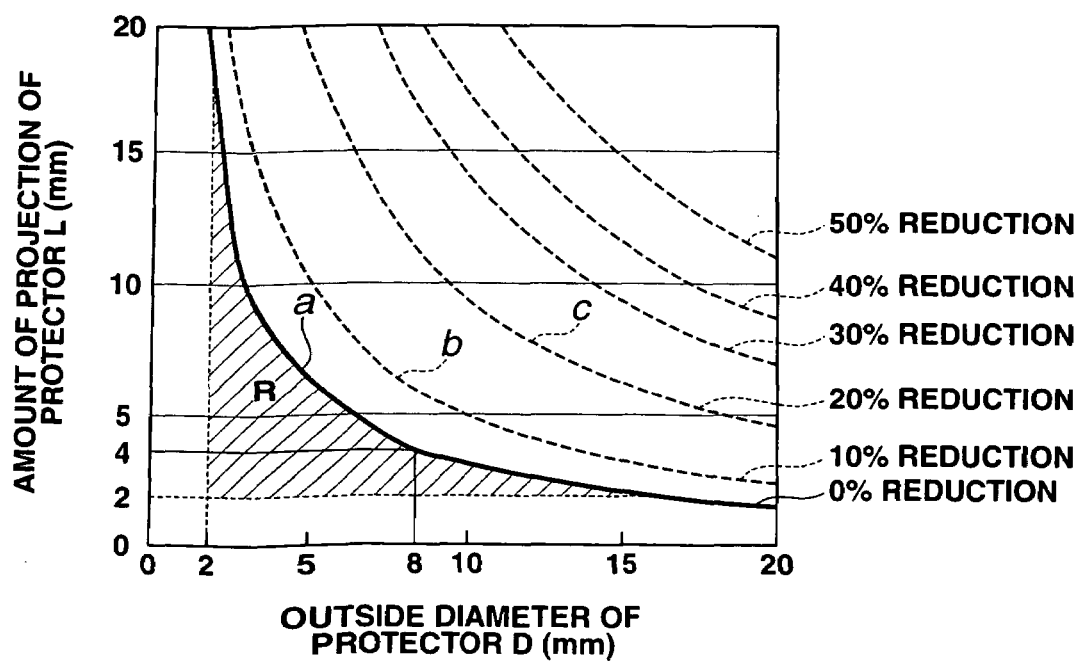
FIG. 3 is a drawing showing reduction curves of exhaust efficiency with respect to an outside diameter of the protector and the projection amount of protector, according to the one embodiment.

FIG. 1 is a sectional view of an oxygen sensor, under the state where the oxygen sensor is fixed to an exhaust pipe. FIG. 2 is a drawing to explain a relationship between an amount of projection of a protector and response time of the oxygen sensor. FIG. 3 is a drawing showing reduction curves of exhaust efficiency with respect to an outside diameter and the projection amount of the protector.

As shown in FIG. 1, a structure of an oxygen sensor 10 is mainly formed of a sensing element 11 which detects or senses oxygen concentrations in measurement exhaust gas that flows in an exhaust pipe 1, and a tubular or cylindrical shaped protector 12 which covers an outside of sensing element 11 and whose top end portion projects or protrudes toward an inside of exhaust pipe 1. In mote detail, sensing element 11 penetrates a core portion of a holder 13 with air tight structure. As for protector 12, its top end portion 12a is closed (in fact, after-mentioned inflow hole or opening 12c is formed at the top end portion 12a), and protector 12 covers an end portion of sensing element 11. A base end portion 12b of protector 12 is connected with holder 13 with air tight structure.

Oxygen sensor 10 is fixed or attached to exhaust pipe 1 as follows. Protector 12 (also, with sensing element 11 and holder 13) is first inserted from its top end portion 12a into an opening portion 1a that is formed on an inner wall of exhaust pipe 1, and then holder 13 screws into a screw portion or thread portion 2a of a cylindrical boss portion 2 that protrudes from an outer wall of exhaust pipe 1 concentrically with opening portion 1a, with air-tightness.

With respect to size of oxygen sensor 10, in this case, it is preferable that the size is reduced to the extent of an outside diameter of 14 [mm] of holder 13. And also, it is preferable that a thread diameter of screw portion 2a of cylindrical boss portion 2, into which holder 13 screws, is smaller than or equal to 10.

In FIG. 1, although an upper portion of oxygen sensor 10 from the halfway of holder 13 is omitted, the upper portion is provided with a lead wire that is connected to sensing element 11. The oxygen concentrations detected by sensing element 11 are converted into electronic signals and then are output from the lead wire to an external part.

As mentioned above, inflow hole 12c is formed at a projecting portion of protector 12 which projects or protrudes inside exhaust pipe 1 so as to introduce the exhaust gas. The exhaust gas flowing into inflow hole 12c is supplied to sensing element 11, and thus the oxygen concentrations are detected. Further, this exhaust gas flowing into protector 12 returns to the inside of exhaust pipe 1 from an ejection or discharge hole (not shown).

Here, in a case where the oxygen sensor 10 having the above structure is used inside exhaust pipe 1 of a small displacement internal combustion engine that is mounted on motorcycle etc, on the whole, a diameter K of a flow passage of the exhaust pipe 1 is designed to be about 40 [mm]. And then, as shown in FIG. 1, an outside diameter D of protector 12 and a projection amount L of protector 12 inside exhaust pipe 1 are set so that oxygen sensor 10 can obtain good response time at the detection of the oxygen concentrations while restricting a resistance of an exhaust gas flow to a small value.

These projection amount L and outside diameter D of protector 12 are defined as follows. The projection amount L is defined as a length from an inner peripheral surface of exhaust pipe 1 to a top end of protector 12. The outside diameter D is defined as a maximum outer diameter of protector 12 protruding inside exhaust pipe 1.

In FIG. 2, a measurement result of a relationship between the projection amount L and the response time of oxygen sensor 10 is shown. In the measurement, the projection amount L is changed by 2 [mm] within a range from 2 [mm] to 12 [mm] and the response time of oxygen sensor 10 is measured versus the projection amount L. As a result of two measurements, as can be seen in FIG. 2, in either case, when the projection amount L is 2 [mm], the response time becomes long (namely that responsiveness deteriorates). On the other hand, when the projection amount L is 4 [mm], the response time becomes short (namely that responsiveness improves). Further, when the projection amount L is between 4 [mm] and 12 [mm], the response time is substantially constant.

In this experiment shown in FIG. 2, the projection amount L is greater than or equal to 2 [mm]. The reason why the projection amount L is greater than or equal to 2 [mm] is as follows. In a case where exhaust pipe 1 bends (especially, exhaust pipe 1 bends upstream thereof), the exhaust gas is susceptible to viscosity of the gas at around the inner peripheral surface of the exhaust pipe 1. Gas concentration of high viscous gas such as NO (nitrogen oxides) particularly deviates or differs from a center of gas flow. Because of this, in order to prevent this, at least 2 [mm] is required as the projection amount L of protector 12.

Further, regarding sensing element 11, cell function of fixed electrolyte (ZrO2) that forms this sensing element 11 needs not only function of ionic conduction of YSZ (Y2O3 mixture ZrO2=solid electrolyte) but also function of ionic reaction of inner and outer electrodes and catalysis or catalytic action of the outer electrode. Because of this, in order to reduce internal resistance and to increase an activity of the sensor, a measure of cross-sectional area is required.

Furthermore, in theory, the solid electrolyte itself functions as long as there are bonds of several molecules. However, in order to use electrode reaction (ionization reaction) and catalytic reaction with efficiency, it is required that a contact or touch area with the solid electrolyte and a contact area with the exhaust gas be secured properly and reasonably. In this embodiment, a required minimum lateral area of sensing element 11 is greater than or equal to 5 [mm2]. Therefore, if the projection amount is set to 2 [mm], a lateral length of 2.5 [mm] is required. That is, an outside diameter of sensing element 11 becomes 0.8 [mm] at this time. However, in fact, there is a needless area of about 20%.

For this reason, the outside diameter of sensing element 11 requires at least 1 [mm] or longer.

As described above, in the case where the outside diameter of sensing element 11 is 1 [mm] or longer, the outside diameter D of protector 12 requires at least 2 [mm] or longer. That is to say, protector 12 serves to introduce the exhaust gas into an inner space thereof and supply it to sensing element 11 while concentrating the exhaust gas. For this reason, a length of 0.3 [mm] of the inner space is required as a minimum inner space. Accordingly, an actual outside diameter D of protector 12 becomes 2 [mm] from the following calculation. D=1 (the outside diameter of sensing element 11)+0.3 (the space)×2+0.2 (thickness of protector 12)×2=2 [mm].

Consequently, the above condition, namely that the outside diameter D is greater than or equal to 2 [mm] and the projection amount L is greater than or equal to 2 [mm], is obtained. Then, an experiment for verifying a relationship between an exhaust efficiency and the outside diameter D and projection amount L was carried out within the above area (condition) (the outside diameter D≧2 [mm] and the projection amount L≧2 [mm]). As a result, as shown in FIG. 3, reduction curves or characteristic of the exhaust efficiency are obtained ("a" is 0% reduction, "b" is 10% reduction, "c" is 20% reduction, . . . ).

In FIG. 3, an area R indicated by hatching is an area where the following three areas overlap each other; an area where the outside diameter D is greater than or equal to 2 [mm], an area where the projection amount L is greater than or equal to 2 [mm] (preferably greater than or equal to 4 [mm]), and an area where the reduction of exhaust efficiency is substantially smaller than or equal to 0%. And this area R is an optimum area having good response time and no resistance of the exhaust gas flow.

When the projection amount L of 4 [mm] of protector 12, which is obtained from the above result of FIG. 2, is applied to this optimum area R, an effective or significant maximum outside diameter D of protector 12 becomes 8 [mm] that is plotted out on the reduction curve "a" of 0% reduction of the exhaust efficiency.

Consequently, the following conditions are derived from the above experiment. On the reduction curve "a" of 0% reduction of the exhaust efficiency, $$D \times L = 8\ [\text{mm}] \times 4\ [\text{mm}] = 32\ [\text{mm2}] \quad (1)$$

Regarding the optimum area R, $$D \times L < 32\ (\text{here}, D \geqq 2\ [\text{mm}]\ \text{and}\ L \geqq 2\ [\text{mm}]) \quad (2)$$

Here, the exhaust efficiency of exhaust pipe 1 is fixed depending on the degree or extent of protrusion of protector 12 according to the size of exhaust pipe 1. That is, the exhaust efficiency is fixed in accordance with a ratio of "D×L" of protector 12 to a cross-sectional area S of the flow passage of exhaust pipe 1 in this embodiment, since the internal or bore diameter K of exhaust pipe 1 is set to 40 [mm], the cross-sectional area S of the flow passage of exhaust pipe 1 is $S = 20 \times 20 \times \pi \approx 1256$ [mm2]. On the other hand, D×L=32 [mm2] from the expression (1). Thus the ratio is (D×L)/S=32/1256≈0.025. That is to say, in this embodiment, the outside diameter D of protector 12 and the projection amount L of the protector 12 inside exhaust pipe 1 are set so that the ratio of the product of the outside diameter D and the projection amount L (D×L) to the cross-sectional area S of the flow passage of exhaust pipe 1 becomes substantially smaller than or equal to 2.5%.

As described above, in the case of the bore diameter K of 40 [mm] of exhaust pipe 1, the value of the product of the outside diameter D and projection amount L (D×L) is set to 32 or smaller (D×L≦32). However, in a case also where the bore diameter K of exhaust pipe 1 differs from 40 [mm], it became evident from a detailed study and analysis by inventors etc that the same effects can be obtained by setting the ratio of (D×L) to the cross-sectional area S of flow passage of the exhaust pipe to 2.5% or smaller according to the bore diameter.

Further, as is clear from the measurement result of FIG. 2, the response time becomes short and is substantially constant when the projection amount L of protector 12 is set to 4 [mm] or longer. Therefore, it is further preferable that the projection amount L of protector 12 is set to 4 [mm] or longer.

As explained above, in oxygen sensor 10 according to the embodiment, the outside diameter D of protector 12 and the projection amount L of the protector 12 inside exhaust pipe 1 are set so that the ratio of the product of the outside diameter D and the projection amount L (D×L) to the cross-sectional area S of the flow passage of exhaust pipe 1 is substantially within 2.5% or smaller. It is therefore possible to secure a sufficient quantity or amount of introduced gas for sensing the oxygen concentration and to improve the responsiveness of oxygen sensor 10 without increasing the gas flow resistance of the exhaust gas flowing in exhaust pipe 1.

Especially in the case of the bore diameter of 40 [mm] of exhaust pipe 1, by setting the value of the product of the outside diameter D [mm] and projection amount L [mm] (D×L) to 32 or smaller (D×L≦32), besides being able to reduce the gas flow resistance in exhaust pipe 1, it becomes possible that oxygen sensor 10 could become compact while securing a required quantity of introduced gas to oxygen sensor 10. And then, for instance, in a case as well where oxygen sensor 10 is applied to exhaust pipe 1 of the small displacement internal combustion engine such as an engine mounted on motorcycle, oxygen sensor 10 has the advantage that its layout becomes easy.

In addition, by setting the projection amount L of protector 12 to 4 [mm] or longer, it is possible to introduce a required quantity of exhaust gas into protector 12 efficiently and to effectively improve the responsiveness of oxygen sensor 10.

In the present invention, the oxygen sensor can be modified as follows with the same workings and effects as the above embodiment. For example, the structure of the oxygen sensor itself (especially the structure of parts other than the shown parts in FIG. 1) is not limited, and a variety of structures can be appropriately used.

As described above, for the oxygen sensor, it is preferable that the projection amount L of the protector is greater than or equal to 2 [mm] and the outside diameter D of the protector is greater than or equal to 2 [mm]. By the above setting, adequate detection accuracy and detection responsiveness for detection of the oxygen concentration can be obtained.

Further, in a case where the projection amount L of the protector is set to 4 [mm] or longer, it is preferable that a forming position of the inflow hole formed at the protector is set within a range between 0 and 4 [mm] from the top end of the protector toward the base end portion of the protector. By this setting, the inflow hole can be formed at the projecting portion of protector, which protrudes inside the exhaust pipe. And thus, it is possible to certainly introduce the exhaust gas into the protector. And in this case, if the inflow hole is formed at the top end of the protector, the detection responsiveness can improve.

Furthermore, in the embodiment, the projection amount L is defined as the length from the inner peripheral surface of exhaust pipe to the top end of protector, and the outside diameter D is defined as the maximum outer diameter of protector protruding inside the exhaust pipe. And both the projection amount L and outside diameter D are set so that the reduction of exhaust efficiency is 0%. However, it is also possible that the reduction of exhaust efficiency is within a predetermined range of reduction rate of the exhaust efficiency, from 1 to 5%. That is, the reduction of exhaust efficiency is not 0% but can be the predetermined reduction rate. In that case, a pressure loss and an increase of the gas flow resistance are allowed to respective amounts corresponding to this predetermined reduction rate of exhaust efficiency. And a shield cross-sectional area (a substantially rectangular projected area) of the projecting portion protruding from the inner peripheral surface of exhaust pipe can be set to a size corresponding to this predetermined reduction rate of exhaust efficiency. Accordingly, in the case where the reduction of exhaust efficiency is set to the predetermined reduction rate other than 0%, the oxygen sensor (the projection amount L and outside diameter D) can be set so that the product of the outside diameter D and projection amount L (D×L) becomes smaller than or equal to the shield cross-sectional area. Or conversely, if the projection amount L and outside diameter D are set so that the product of the outside diameter D and projection amount L (D×L) becomes smaller than or equal to the shield cross-sectional area, the oxygen sensor can be used under the condition where the reduction of exhaust efficiency is within the predetermined range.

By the above setting, besides being able to set the projection amount L and outside diameter D more easily and accurately, design of the oxygen sensor and its peripheral parts and their layout become easy.

This application is based on a prior Japanese Patent Application No. 2005-306274 filed on Oct. 20, 2005. The entire contents of this Japanese Patent Application No. 2005-306274 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. An oxygen sensor comprising:
   a sensing element detecting an oxygen concentration in a measurement gas that flows in a pipe;
   a cylindrical protector which covers an outside of the sensing element and whose top end portion projects toward an inside of the pipe, and
   an outside diameter D of the protector and a projection amount L of the protector inside the pipe being set so that a ratio of the product of the outside diameter D and the projection amount L (D×L) to a cross-sectional area S of a flow passage of the pipe becomes substantially smaller than or equal to 2.5%.

2. The oxygen sensor as claimed in claim 1, wherein:
   when an internal diameter of the pipe is smaller than or equal to 40 mm, a value of the product of the outside diameter D and the projection amount L is set to 32 $mm^2$ or smaller.

3. The oxygen sensor as claimed in claim 2, wherein:
the projection amount L of the protector inside the pipe is set to 4 mm or greater, and in this case, the outside diameter D of the protector is set to 8 mm or smaller.

4. The oxygen sensor as claimed in claim 2, wherein:
the projection amount L of the protector is defined as a length from an inner peripheral surface of the pipe to a top end of the protector, and
the outside diameter D of the protector is defined as a maximum outer diameter of the protector projecting inside the pipe.

5. The oxygen sensor as claimed in claim 2, wherein:
the setting of the projection amount L of the protector is applied in a case where the pipe, to which the protector is attached, bends upstream of the pipe.

6. An oxygen sensor set inside an exhaust pipe for a motorcycle comprising:
a sensing element detecting an oxygen concentration in a measurement gas that flows in the exhaust pipe;
a cylindrical protector which covers an outside of the sensing element and whose top end portion projects toward an inside of the exhaust pipe, and
when an internal diameter of the exhaust pipe is smaller than or equal to 40 mm, an outside diameter D of the protector and a projection amount L of the protector inside the exhaust pipe being set so that a ratio of the product of the outside diameter D and the projection amount L (D×L) to a cross-sectional area S of a flow passage of the exhaust pipe becomes substantially smaller than or equal to 2.5%.

7. The oxygen sensor as claimed in claim 6, wherein:
a value of the product of the outside diameter D and the projection amount L is set to 32 $mm^2$ or smaller.

8. The oxygen sensor as claimed in claim 7, wherein:
the projection amount L of the protector inside the exhaust pipe is set to 4 mm or greater, and in this case, the outside diameter D of the protector is set to 8 mm or smaller.

9. The oxygen sensor as claimed in claim 7, wherein:
the projection amount L of the protector is defined as a length from an inner peripheral surface of the exhaust pipe to a top end of the protector, and
the outside diameter D of the protector is defined as a maximum outer diameter of the protector projecting inside the exhaust pipe.

10. The oxygen sensor as claimed in claim 7, wherein:
the setting of the projection amount L of the protector is applied in a case where the exhaust pipe, to which the protector is attached, bends upstream of the exhaust pipe.

* * * * *